United States Patent [19]

Pery et al.

[11] 4,203,893

[45] May 20, 1980

[54] COUPLING PRODUCTS OF CYTIDINE-DIPHOSPHOCHOLINE AND AMINO-COMPOUNDS FOR PHARMACEUTICAL USE

[75] Inventors: Pierre Pery, Villepreux; Gérard Luffau; Joelle Poulain nee Charley, both of Plaisir; Agnes Petit, Thiverval Grignon, all of France

[73] Assignee: Institut National de la Recherche Agronomique, Paris, France

[21] Appl. No.: 937,972

[22] Filed: Aug. 30, 1978

[30] Foreign Application Priority Data

Sep. 7, 1977 [FR] France .................. 77 27151

[51] Int. Cl.$^2$ .................. C08H 1/00; A61K 37/02
[52] U.S. Cl. .................. 260/121; 435/181; 260/6; 260/112 R; 260/112.5 R; 260/115; 260/117; 260/123.5; 424/86; 424/87; 424/89; 424/92; 528/328; 525/419
[58] Field of Search ............ 260/121, 112 R, 112.5 R, 260/115, 117, 123.5, 6; 195/63; 528/311, 328; 424/86, 87, 89, 92

[56] References Cited

PUBLICATIONS

Gurr et al., Chemical Abstracts, vol. 61:11,088g (1964).
Lee et al., Nature, vol. 247 (Jan. 1974) pp. 55–57.

*Primary Examiner*—Walter C. Danison
*Attorney, Agent, or Firm*—Hammond & Littell, Weissenberger and Muserlian

[57] ABSTRACT

The products of the invention are obtained by a method which consists of: oxidizing cytidine-diphosphocholine, fixing the dialdehyde obtained by the preceding oxidation of the ribose of the cytidine on $NH_2$ groups of the amino compound in alkaline aqueous solution, stabilizing the coupling thus formed by reduction and recovering the macromolecular product thus obtained in the form of an aqueous solution. The latter can be freeze-dried to provide a powder suitable for preservation. The coupling occurs between the oxidized ribose groups of the cytidine-diphosphocholine and the lysine residues of the amino compounds. The products of the invention are suitable as vaccines against parasites belonging to the class of those including molecules bound to a phosphorylcholine residue, such as intestinal or respiratory parasites.

7 Claims, No Drawings

COUPLING PRODUCTS OF CYTIDINE-DIPHOSPHOCHOLINE AND AMINO-COMPOUNDS FOR PHARMACEUTICAL USE

BACKGROUND OF THE INVENTION

1. Field of the Invention

The present invention relates to coupling products of cytidine-diphosphocholine and amino compounds; it relates also to a process for producing these products and their use, notably their pharmaceutical use, in particular as vaccines.

2. Description of the Prior Art

Phosphorylcholine is a simple compound which is bound in nature to lipids, polyosides and proteins. Tests have in fact shown that extracts of various stages of development of several nematodes: *Nippostrongylus brasiliensis* (parasite of the rat), *Haemonchus contortus* (parasite of the sheep), undetermined nematodes of the respiratory system of the pig and *Heligmosomoides polygyrus* (parasite of the mouse) contained macromolecular compounds carrying phosphorylcholine; these compounds can be demonstrated by myelomes in the mouse as possessing anti-phosphorylcholine antibody activity; for this purpose reference may be made to the article of PERY et al in European Journal of Immunology vol. 4, 1974, pp. 637–639.

The immunochemical study of the macromolecular compound bearing phosphorylcholine, obtained from *Nippostrongylus brasiliensis* and purified, has shown an antigene determinant common to all the extracts tested (PERY et al. 1975 b. Ann. Immunol. (Institut Pasteur) 126 C 355).

In addition, tests have shown that the injection by the intradermal route of 10 µg of the above purified compound to rats, eight days before infestation, is manifested by a modification of the transit of the larvae into the lungs and by a decrease in the number of parasites dwelling in the intestine before autosterilization (PERY et al. 1975 a C.R. Acad. Sc. Paris 281 series D 203–306).

It has already been proposed to prepare conjugated products between proteins and compounds bearing phosphorylcholine groups. Thus J. Schroer and J. M. Davie in "The Journal of Immunology" Vol. 118, No. 6, 1987–94 (1977) have described the coupling of phosphorylcholine with hemocyanine and identify the fractions of antigene formed on the injection of these conjugates into guinea pigs. In the same way W. Lee, H. Cosenza and H. Kohler have described in "Nature", Vol. 247 4 January 1974, the coupling of p-diazo phenylphosphorylcholine with the tyrosine residues of proteins, such as hemocyanine or the flagellae of salmonellose. The same authors have studied the immunitary response of mice to the injection of these conjugates.

However, the syntheses of the conjugated products of the prior art, bearing phosphorylcholine groups, are complicated and the starting compounds are difficult to obtain. In addition, the coupling is done through tyrosine residues of proteins which therefore limits the generality of the coupling technique and the number of phosphorylcholine groups which can be fixed to one mole of protein.

It is an object of the invention to provide processes and products which remove these drawbacks of the prior art.

GENERAL DESCRIPTION OF THE INVENTION

It has now been found that it is possible to obtain by synthesis, products based on phosphorylcholine which constitute chemically defined artificial antigenes.

The products according to the invention are coupling products based on amino compounds carrying phosphorylcholine groups; they are useful as anti-parasite vaccines. Another application of the compound according to the invention is in the field of the discovery, the purification and the measurement of biological compounds reacting with phosphorylcholine, that is to say, reactive protein C and anti-phosphorylcholine antibodies.

The products according to the invention are produced by coupling between cytidine diphosphocholine and amino compounds. The process according to the invention for obtaining these coupling compounds consists of reacting cytidine-diphosphocholine with amino compounds after oxidation, according to the technique developed by ERLANGER and BEISER for the fixing of ribonucleotides on proteins (1964, Proc. Nat. Acad. Sci. USA, 52, 68–74).

In a more detailed form, the process according to the invention comprises the following steps which consist of:

(1) oxidizing cytidine-diphosphocholine;
(2) fixing the dialdehyde, obtained by the preceding oxidation of the ribose of the cytidine, on the $NH_2$ groups of the amino compound in alkaline aqueous solution;
(3) stabilizing the coupling thus formed by reduction;
(4) recovering the macromolecular product thus obtained in the form of an aqueous solution, the latter being lyophilisable to provide a powder suitable for preservation.

The amino compounds which are suitable for the purposes of the present invention are compounds which contain free $NH_2$ groups or compounds on which it is easily possible to fix lysine; these are for example proteins, synthetic peptides, or amino polysaccharides. By way of example of suitable amino compounds, may be mentioned the albumines of the various animal species, notably human albumin serum, ovalbumin, gelatin, lectins such as concanavaline A, hemocyanine, limulus, bacterial bodies, flagellae of salmonellae, bacteriophages, viruses, enzymes, polymers of lycine having a degree of polymerization higher than 2, synthetic polymers of amino acids having several lysine residues. Among the compounds not bearing amine residues $NH_2$, but on which lysine can easily be branched, may be mentioned polysaccharides such as dextrans, levans and polymers of sucrose and epichlorhydrin, such as, for example, the product known by the trade name "FICOLL" (manufactured by Pharmacia Fine Chemicals, Uppsala, Sweden) and other similar compounds. When a compound not including free $NH_2$ groups is applied, but on which it is possible to fix lysine easily, such as a polysaccharide for example, first there is carried out the fixing of n-lysine to the compound to obtain an n-lysine polysaccharide and then the coupling reaction according to the invention is carried out between the polysaccharide n-lysine and the cytidine-diphosphocholine.

The oxidation of the ribose of cytidine-diphosphocholine may advantageously be carried out with sodium periodate. It is convenient to use an excess of oxidizing agent with respect to the cytidine-diphosphocholine to be oxidized; the excess oxidizing agent can then easily be removed, for example by decomposition.

The alkaline aqueous solution of the amino compound applied in step 2 of the process according to the invention has a pH comprised between about 9 and 9.5; the pH of the aqueous solution is advantageously adjusted to the above value by means of 5% sodium carbonate.

The coupling thus produced is then stabilized by reduction; as a suitable reducing agent sodium borohydride or any other similar compound may be mentioned.

The macromolecular product formed is then separated from the reactants, for example by gel chromatography and finally is advantageously lyophilized.

The number of moles for cytidine-diphosphocholine per mole of amino compound depends on the amino compound concerned; in general this number of moles is less than or equal to the number of $NH_2$ groups in the amino compound. In the case of human albumin serum the ratio of the phophorylcholine residues to the number of moles of human albumin serum is advantageously comprised between 1 and 30.

The products of the invention are coupling products of cytidine-diphosphocholine and amino compounds selected from among the compounds bearing free-$NH_2$ groups and compounds on which lysine can be fixed, the coupling bond being formed, after oxidation of the cytidine-diphosphocholine, between the oxidized ribose groups of the latter and the lysine residues of said amino compounds.

The invention uses as a starting material cytidine-diphosphocholine which is a substance available commercially and inexpensive. Contrary to the prior art, the process of the invention involves a small number of steps. It is easily convertible to the industrial scale. Not requiring the application of a volatile solvent, it avoids additional and expensive steps of evaporation or subsequent removal of this solvent, for example acetonitrile or pyperidine.

Cytidine-diphosphocholine is also a compound of known structure, which is an intermediate in the synthesis of lecithins and of sphingo-myelins. The conjugated products, prepared according to the invention from cytidine-diphosphocholine, are decomposable in vivo; hence they do not result in any secondary action since they are usable in the normal metabolism of the cells. On the other hand, the conjugated products of the prior art, which are obtained, for example, from p-diazo-phenylphosphorylcholine, may result in undesirable reactions in a living organism.

The products of the invention are characterized by the fact that the coupling is made through lysine residues of the amino compounds, whereas in the prior art, the fixing was effected by tyrosine groups. The lysine groups are generally more numerous in amino compounds than tyrosine groups, which enables, according to the invention, the fixing of more phosphorylcholine groups on a given amino compound.

The coupling products according to the invention are also characterized by (1) their molecular weight which is close to that of the support compound due to the fact that the molecular weight of the cytidine-diphosphocholine is very low with respect to those of the support compounds;

(2) their electrophoretic mobility which is more rapid than that of the support compound at pH 8.6. In fact, it is noted, due to the immunoelectrophoreses revealing the antigenes of the support molecule, that there is an increase in the speed of migration as a function of the degree of substitution of the compound;

(3) their absorption spectrum in ultraviolet light; the U.V. spectra of the proteins possess two characteristic wave lengths which permit the degree of coupling to be determined: 280 nm (absorption of the tyrosine and phenyl-alanine groups of the proteins); 260 nm (absorption of the cytosine of the cytidine diphosphocholine); and (4) their average content of phosphorylcholine residues per molecule of support compound.

The characteristic (3) above enables exact measurement of the degree of coupling obtained, by simple comparison of the U.V. spectra of the amino compound on the one hand and of the conjugated product on the other hand.

It will also be noted that the process of the invention is applicable very generally, not only to proteins, but also to amino compounds other than proteins, the sole condition being that it be possible to fix lysine on these compounds. The invention hence enables a great variety of couplings.

As has been previously indicated, the coupling products of the invention are useful as anti-parasite vaccines.

The study of the physiopathology of animal parasites and the acquisition of resistance to reinfestation (either following a primary infestation, or following vaccination) is difficult, when the experiment is carried out on domestic animals. However, it has been found that the development cycle of certain parasites, such as for example, *Nippostrongylus brasiliensis*, the parasitic nematode of the intestine of the rat, has great analogies with that of certain of domestic animal parasites. The coupling products according to the invention have hence been tested in the rat.

The rat is capable, at the end of some ten days, of stopping the laying of the eggs of adult female parasites *Nippostrongylus brasiliensis*, then of freeing itself of its population of intestinal worms. This phenomenon of autosterilization is considered as the first manifestation of immunity created in the host by the parasite. The mechanism of autosterilization seems complex and apparently necessitates the conjugated action of the antibodies and of the immune lymphoid cells.

A second infestation of rats after autosterilization shows that the latter become resistant to the parasite.

This resistance may be produced following infestation by a very small amount of infesting larvae (LUF-FAU et al. 1975 Ann. Immunol. (Institut Pasteur) 126 C 354).

It has been found that the administration of coupling products according to the invention to rats twelve days before infestation by the *Nippostrongylus brasiliensis* results in a considerable decrease in the eggs emitted daily during the period of reproduction of the parasites and a decrease also considerable of the adult worms contained in the intestine in the course of the period preceding autosterilization.

This protection is specific to phosphorylcholine, since the rats having received the same doses of unsubstituted albumin serum are as sensitive as the controls, and it is produced homogeneously in all rats suitably treated.

The tests related below show that the coupling products according to the invention have a vaccinating role against the parasites belonging to the class of those including molecules bound to a phosphorylcholine residue; generally intestinal or respiratory parasites are involved. The products of the invention are hence capable of being used as anti-parasite vaccines for domestic animals and man, taking into account the analogy between the development of *Nippostrongylus brasiliensis* and certain domestic animal parasites which were considered above.

The doses of the coupling product phophorylcholine-amino compounds according to the invention, which are suitable by way of anti-parasite vaccines, vary according to the parasite and the amino compound coming into play in the coupling.

However, it may be indicated that these doses are generally low and of the order of some micrograms.

By way of example, it is indicated that the coupling product cytidine-diphosphocholine-human albumin serum may be used at doses ranging from 20 to 80 μg per rat.

The invention relates therefore also to anti-parasite vaccines containing, by way of active principle, an effective amount of a coupling product according to the invention in combination with a suitable pharmaceutically effective vehicle. Among the vehicles which are suitable for the purposes of the invention, may be mentioned physiological serum and all aqueous buffers.

In addition, the vaccine containing a coupling product according to the invention may be administered in a coated form, such as a form in capsules or in liposomes.

The vaccines according to the invention may be administered by the intradermal route, the oral route or in aerosol form.

The coupling products cytidine-diphosphocholine-amino compounds of the invention are also useful as measuring reactants in discovery techniques, purification and measurement of particle compounds reacting with phosphorylcholine, that is to say reactive protein C and anti-phosphorylcholine antibodies.

The introduction of a compound bearing phosphorylcholine in an animal or in man can result in the synthesis by the organism of anti-phosphorylcholine antibodies which could be shown in the serum of infested subjects. (LEE et al. 1974, Nature, 247,55-57).

These anti-phosphorylcholine antibodies are not the only substances developed by the organism which are capable of reacting with compounds including phosphorylcholine. In fact, it has been shown for a long time that the serum of individuals afflicted with different affections containing a mobility protein β, which has been called reactive protein C, since it possessed the ability of being precipitated by the C polysaccharide of the pneumococcus. It has been shown that the reaction between the reactive protein C and the pneumococcus polysaccharide was due to the presence on the latter of phosphorylcholine residues (VOLANAKIS and KAPLAN 1971, P.S.E.B.M., 136, 612-614).

The reactions of the reactive protein C and of the anti-phosphorylcholine antibodies with the compounds bearing phosphorylcholine are very close and give birth to precipitates, agglutinates, flocculates according to the type of reaction used.

It has been found that the coupling products cytidine-diphosphocholine—amino compounds may be combined with the substances sought in biological liquids and thus anable measurement of the substance.

Thus, the coupling products cytidine-phosphocholine-aimino compounds enable, by using buffers containing 0.01% of calcium chloride, to discover research products, namely reactive protein C and anti-phosphorylcholine antibodies by double immunodiffusion reactions, by the ring test, and the flocculation test.

Reactions of the coupling products cytidine-diphosphocholine-amino compounds with reactive C protein may be inhibited by 5% trisodium nitrate, the product known under the commercial name "Anaklepton" $5.10^{-3}M$, cytidine-5'-diphosphocholine or phosphorylcholine $10^{-3}M$, whereas only the two latter compounds inhibit the reaction of the coupling products of the invention with antiphosphorylcholine antibodies, which enables both differential discovery and verification of the specificity of the reaction.

It is also possible to obtain, by the insolubilization techniques described for affinity chromatography, a derivative useful for detecting compounds reacting with phosphorylcholine in biological fluids. The citrate or the "Anaklepton" enabling the release of purified reactive C protein thus in a single step, and the phosphorylcholine added subsequently enables the recovery of the anti-phosphorylcholine antibodies.

The utilization of the substituted proteins in affinity chromatography enables purification very rapidly of large amounts of reactive C protein and of anti-phosphorylcholine antibodies which could be freeze-dried to serve as a measuring standard for the quantitative measurement described below.

By current techniques of immunology, it is possible to measure the reactive C protein and the anti-phosphorylcholine antibodies with the coupling products according to the invention. It is possible notably to utilize the following techniques:

—the turbidimetry or nephelometry which consists of measuring the cloudiness appearing in the course of the reaction of the product sought;

—simple radical immunodiffusion by using the inverse system described by VAERMAN et al (1969, Immunochemistr 6 287-293) enabling by integrating the coupling product according to the invention in a suitable support (gelose, agarose, paper, cellulose acetate) precipitation zones to be produced whose final diameter is directly proprotional to the amount of reactive C protein or anti-phosphorylcholine reacting;

—the fixing of the coupling product according to the invention on red blood cells enables passive hemoglutination reactions to be carried out. The treatment with glutaraldehyde of red blood cells before or after the fixing of the product of the invention enables them to be freeze-dried and to be obtained in an easily usable form.

The present invention therefore also relates to measuring reactants of biological compounds reacting with phosphorylcholine; these reactants contain a coupling product according to the invention fixed on sheep's red blood cells if necessary treated with glutaraldehyde, and the coupling product can if necessary be activated by glutaraldehyde before or after fixation. The invention also relates to a measuring reactant in the form of gelose containing a coupling product according to the invention.

DESCRIPTION OF PREFERRED EMBODIMENTS

The invention will now be described in more detail in the illustrative but non-limiting examples given below.

EXAMPLE 1 preparation of cytidine-diphosphocholine-protein coupling products

The general technique of coupling cytidine-disphosphocholine to proteins is as follows:

Cytidine-diphosphocholine in a variable amount was oxidized by 2.5 ml of 0.1 M sodium periodate, for 20 minutes at ambient temperature. The excess of periodate was decomposed by the addition of 0.15 ml of molar ethylene glycol which was allowed to act for 5 minutes at ambient temperature.

140 mg of the protein concerned was dissolved in 10 ml of distilled water brought to pH by 9.5 by 5% sodium carbonate and the oxidized cytidine-diphosphocholine was made to react with this protein.

The fixation reaction of the dialdehyde obtained by periodic oxidation of the ribose of the cytidine on amino groups of protein was pursued for 45 minutes at pH 9-9.5.

The bond was then stabilized by reduction with sodium borohydride for one night (75 mg of sodium borohydride were dissolved in 10 ml of distilled water and added to the preparation).

The stability of the bond was tested at an acid pH; 5 ml of molor formic acid were added for one hour, then the pH of the solution was adjusted to 8.5 with molar ammonia.

The macromolecular product obtained was separated from the reactants by salting out on a "Biogel P 30" column of ammonium bicarbonate and then freeze-dried.

This technique was used with success to couple cytidine-diphosphocholine to the following proteins: human albumin serum, gelatin, convanavalin, hemocyanin.

EXAMPLE 2

The following products, named by abreviation PC-HSA modified by an index, were synthesized from human serum albumin by the operational procedure described previously in Example 1.

| Coupling product obtained | cytidine-diphosphocholine (in g) | human serum albumin (in g) |
|---|---|---|
| PC HSA$_0$ | 90 | 140 |
| PC HSA$_1$ | 45 | 140 |
| PC HSA$_2$ | 15 | 140 |
| PC HSA$_3$ | 6 | 140 |
| PC HSA$_4$ | 3 | 140 |
| PC HSA$_5$ | 1.5 | 140 |

The compounds obtained were analysed by chromatography on a "Sephadex G100" column; it was found that they were not contaminated by free cytidine-diphosphocholine.

The degree of substitution, determined by measurement of the ultraviolet light absorption due to the cytidine-diphosphocholine on the one hand and to the albumin on the other hand was as follows:

| PC HSA$_0$: | 21 moles of cytidine-diphosphocholing per molecule of albumin | | | | | |
|---|---|---|---|---|---|---|
| PC HSA$_1$: | 15 | — | — | — | — | — |
| PC HSA$_2$: | 5 | — | — | — | — | — |
| PC HSA$_3$: | 3 | — | — | — | — | — |
| PC HSA$_4$: | 2 | — | — | — | — | — |
| PC HSA$_5$: | .1 | — | — | — | — | — |

By using 140 mg of concanavalin A or hemocyanin and 90 mg of cytidine-diphosphocholine, the following products have been synthesized: PC concanavalin A (20 phosphorylcholine residues per mole of concanavalin A) and PC hemocyanin (70 residues of phosphorylcholine per per mole of hemocyanin).

EXAMPLE 3

Use of the cytidine-diphosphocholine-human albumin serum coupling products as measuring agents The reactions of the compounds prepared according to Example 1 with the anti-phosphorylcholine antibodies or albumin anti-serum were carried out according to the two following techniques:

—double immunodiffusion on gelose (Ouchterlony O. Progress in Allergy. S. KARGER Basel 1958. 5, 1.)

—passive hemagglutination after fixation of the compounds on sheep's red blood cells (S. LEMIEUX et al. Immunochemistry 1974, 11, 261-269).

The two techniques gave identical results:

—all the compounds reacted similarly with albumin anti-serum antibodies; hence it follows that the phosphorylcholine residues do not interfere with the recognition of the serum albumin determinants.

The PC HSA$_0$ and PC HSA$_1$ compounds reacted in the same manner with anti-phosphorylcholine antibodies or reactive C protein, whereas the compound PC HSA$_2$ reacted less well, and the compounds PC HSA$_{3,4,5}$ did not react, doubtless on account of too low a degree of substitution to give rise to a system detectable by the techniques used.

The compound PC HSA$_0$, the most substituted, was used for semi-quantitative or quantitative serological determinations of the anti-phosphorylcholine antibodies or reactive C protein content which are the two serum proteins reacting with the phosphorylcholine unit.

Stable reactants suitable for practical applications were obtained:

—by fixation of the PC HSA$_0$ to sheep's red blood cells treated with glutaraldehyde in conventional manner;

—by fixation of the activate PC HSA$_0$ with glutaraldehyde on sheep's red blood cells subjected or not to subsequent treatment with glutaraldehyde;

—by the preparation of gelose plates containing PC HSA$_0$ to practice the reversed Mancini method which consists of causing the sera to be tested to migrate in this VAERMAN et al gel (1969, Immunochemistry 6 287.293).

By means of the ascites liquid from a murin myeloma secreting a paraprotein, having an anti-phosphorylcholine activity, from mouse serum whether normal or immunized against other antigenes, specificity of the hemagglutination tests practiced with various types of sheep's red blood cells mentioned above and of the Mancini test was verified, and amounts of antibodies of the order of $9 \times 10^{-7}$ mg/ml, namely about 1 pg/ml, were detectable.

Human sera coming from the Beclere hospital at Clamart were classified in two categories: those which contained reactive C protein and those which were devoid of it, and it was checked that the square of the diameter of the precipitation ring, obtained by the Mancini technique, was proportional to the concentration of this protein.

Discrimination between the two categories of proteins can easily be done since the reaction of demonstrating and measuring the reactive C protein does not take place in the absence of $Ca^{++}$ ions.

These tests can hence be utilized in practice, by proceeding by comparison between the serum to be tested and a well characterized control serum. A hemagglutination reaction can be read after 2 hours and a Mancini test after 48 hours.

Coupling product obtained according to the operational method described in Example 1 were also obtained from hemocyanin, from concanavalin A (see Example 2), from the limula and from gelatin.

These compounds gave the same serological results as PC $HSA_0$; the choice of the phosphorylcholine carrier molecules for the serological reactions is hence completely indifferent, only the degree of substitution counting, which theoretically must be equal to or greater than 2. It was however observed that experimentally the compounds bearing at least 5 phosphorylcholine residues or more were suitable as measuring reactants in the particular case of human albumin serum.

EXAMPLE 4

Preparation of coupling products of cytidine-phosphocholine with compounds on which lysine can easily be fixed The product known by the commercial name FICOLL was used and firstly lysine was fixed to this product by reacting substantially equal amounts by weight of lysine and FICOLL; the product resulting was then treated by the operational method described in Example 1 in order to fix the phosphorylcholine groups on this product.

The operational method described above was followed using as a starting material dextran of about 500,000 molecular weight.

The coupling compounds obtained above gave positive serological results by immunoprecipitation on gelose.

EXAMPLE 5

Protection of rats following medicinal prophylaxis by means of coupling products of the invention Rats received, by stomach incubation by means of a canula possessing an olive shaped end, 0.5 ml of a physiological solution containing a coupling product of the invention. Eight days later, they were infested, by the subcutaneous route, with 3,000 larvae of the infesting stage $L_3$ of the parasite *Nippostrongylus brasiliensis*. This parasite remained, in the adult state, in the small intestine of the rat and persisted there up to the tenth day after infestation.

The conventional manifestations of immunity were:
— stopping of the laying of the female parasites;
— premature expulsion of the adults from the intestine of the rats.

In order to estimate the protection conferred by the products of the invention, the two following tests were therefore proceeded with:
— daily counting of the eggs emitted in the feces of a cage of rats which had undergone the same treatment,
— counting of the worm population of the intestin of each rat 8 days after infestation.

The results of counting the adult worm population in the intestine of the rats was then subjected to statistical calculations to compare the effectiveness of the different treatments.

The following tables summarized the results obtained with PC $HSA_0$.

The rats of Group I received 100 μg of PC $HSA_0$
The rats of Group II received 50 μg of PC $HSA_0$
The rats of Group III received 10 μg of PC $HSA_0$
The rats of Groups IV, V, VI, VII were controls having received serumalbumin or physiological buffer.

In Table I below are indicated the number of eggs per gram of feces; the results of this Table I show that the animals of Group II, which received 50 μg of PC $HSA_0$, excreted many less eggs than the others.

In Table II are indicated the number of worms on autopsy on day 8 after the test infestation; these results show that the animals of Group II harboured less parasites than the others.

All of these results show that 50 μg of PC $HSA_0$ protect the animals whereas 10 or 100 μg does not protect them.

TABLE I

| | Harvest of eggs per gram of faeces | | |
|---|---|---|---|
| | Days after infestation | | |
| GROUP | 6 | 7 | 8 |
| I | 31200 | 120600 | 159800 |
| II | 3850 | 1170 | 23000 |
| III | 36950 | 112500 | 114600 |
| CONTROLS | | | |
| IV | 40750 | 94000 | 103000 |
| V | 44200 | 70400 | 102400 |
| VI | 45950 | 120500 | |
| VII | 51300 | 67900 | 108400 |

TABLE II

| Number of worms on autopsy on the 8th day after test infestation (average) | |
|---|---|
| Group I | 1125 |
| Group II | 206 |
| Group III | 942 |
| Group IV | 874 |
| Group V | 1036 |
| Group VI | 1028 |
| Group VII | 1531 |

In another type of experiment, the five compounds PC $HSA_1$ to PC $HSA_5$ were intubated into groups of rats in the proportion of 10 μg/rat eight days before a test infestation of 3000 infesting larvae.

| Group of treated animals | Coupling product used |
|---|---|
| Group I | PC $HSA_1$ |
| Group II | PC $HSA_2$ |
| Group III | PC $HSA_3$ |
| Group IV | PC $HSA_4$ |
| Group V | PC $HSA_5$ |
| Group VI | Controls |

In Tables III and IV below are indicated respectively the number of eggs excreted per gram of faeces and the number of worms on autopsy on the 8th day after infestation.

These results show that the animals which have received 10 μg of the PC $HSA_5$ compound excreted fewer eggs and harboured less parasites than the other animals; the coupling product PC $HSA_5$ hence conferred better protection at the dose of 10 μg/rat.

These tests show that the doses to be used vary as a function of the degree of substitution of the phosphorylcholine on the human albumin serum.

Tests carried out with the product of coupling hemocyanine-cytidine-diphosphocholine and gelatine-cytidine-diphosphocholine prepared according to Examples 2 and 3 showed that they were active in medicinal prophylaxis.

TABLE III

Excretion of eggs per gram of faeces harvested

| Group | Days after infestation | |
|---|---|---|
| | 7 | 8 |
| I | 56000 | 48800 |
| II | 107600 | 86800 |
| III | 40400 | 86800 |
| IV | 17800 | 40400 |
| V | 4200 | 17800 |
| VI | 75800 | 64400 |

TABLE IV

Number of worms on autopsy on the 8th day after the test

| Group | Number of worms |
|---|---|
| Group I | 757 |
| Group II | 1043 |
| Group III | 1233 |
| Group IV | 560 |
| Group V | 318 |
| Group VI | 1003 |

EXAMPLE 6

The general method described in Example 1 to couple the cytidine-diphosphocholine and ovalbumin was applied. In this way coupling products PC-ovalbumin, usable similarly to those of Example 3 or of Example 5, were obtained.

EXAMPLE 7

The operational method described in Example 1 to couple the cytidine-diphosphocholine and the trypsine inhibitor of soya, was applied. The coupling product obtained found application of the type described previously in Example 3 or 5.

EXAMPLE 8

The operational method as described in Example 1 was applied to couple cytidine-diphosphocholine and killed tuberculous bacillus.

This coupling product found application of the type described previously in Example 3 or 5.

EXAMPLE 9

The operational method described in Example 1 was applied to couple cytidine-diphosphocholine and killed Bordetella pertussis.

These coupling products found application of the type described previously in Example 3 or 5.

The coupling products according to the invention, notably those described in the preceding Examples, are capable of inducing in the animals a synthesis of anti-phosphorylcholine antibodies.

EXAMPLE 10

Cytidine-diphosphocholine activated by sodium periodate results in contact sensitivity of the retarded type when it is administered to the animal by cutaneous painting.

This observation implies the induction of immunity of cellular type.

EXAMPLE 11

The operational method described in Example 1 was applied to couple cytidine-diphosphocholine and Sepharose AH$_2$. This product may be used in a column to purify C reactive protein or anti-phosphorylcholine antibodies in one step from sera containing them. The reactive C protein bound by the compound is released by 5% trisodium citrate, then the anti-phosphorylcholine antibodies were eluted by $10^{-2}$M free phosphorylcholine.

We claim:

1. Coupling products of cytidine-diphosphocholine and amino compounds selected from the group consisting of human albumin serum, ovalbumin, gelatin, lectins hemocyanine, limule, bacterial bodies, salmonellae flagellae, soya, lysine polymers having a degree of polymerization higher than 2, and synthetic polymers of amino acids possessing several lysine residues among compounds bearing free—NH$_2$ groups and compounds on which it is possible to fix lysine selected from the group consisting of polysaccharides and epichlorhydrin polymers, the coupling bond being formed after oxidation of the cytidine-diphosphocholine, under alkaline conditions between the oxidized ribose groups of the latter and the lysine residues of said amino compounds.

2. Products according to claim 1, whose molecular weight is close to that of the starting amino compound and whose electrophoretic mobility at pH 8.6 is faster than that of said compound.

3. Coupling products according to claim 1, having an U.V. absorption spectrum possessing at 260 nm the characteristic wave-length of the cytosine of cytidine-diphosphocholine.

4. Coupling products according to claim 1, obtained by the process consisting of:
   (1) oxidizing cytidine-diphosphocholine;
   (2) fixing the dialdehyde obtained by the preceding oxidation of the ribose of the cytidine, on the NH$_2$ groups of the amino compound in alkaline aqueous solution;
   (3) stabilizing the coupling thus formed by reduction; and
   (4) recovering the macromolecular product thus obtained in the form of an aqueous solution, the latter being lyophilizable to provide a powder suitable for preservation.

5. Coupling products according to claim 4, wherein the oxidation is carried out by means of sodium periodate and the stabilization of the coupling takes place in the presence of a reducing agent, such as sodium borohydride.

6. Coupling products according to claim 1, wherein the amino compound is human albumin serum, wherein the ratio of the residues of the phosphorylcholine to the number of moles of human albumin serum is comprised between 1 and 30, said products being in the form of a powder.

7. The product of claim 1 wherein the polysaccharide is selected from the group consisting of dextrans, levans and sucrose.

* * * * *

UNITED STATES PATENT AND TRADEMARK OFFICE
CERTIFICATE OF CORRECTION

PATENT NO. : 4,203,893
DATED : May 20, 1980
INVENTOR(S) : PIERRE PERY, GERARD LUFFAU, JOELLE POULAIN, AGNES PETIT

It is certified that error appears in the above—identified patent and that said Letters Patent is hereby corrected as shown below:

Column 5, line 64: "anable" should read -- enable --.

Column 6, line 44: "proprotional" should read -- proportional --.

Column 7, line 14: "pH by 9.5" should read -- pH 9.5 --.

Signed and Sealed this

Twenty-first Day of July 1981

[SEAL]

Attest:

Attesting Officer

GERALD J. MOSSINGHOFF
Commissioner of Patents and Trademarks

UNITED STATES PATENT AND TRADEMARK OFFICE
CERTIFICATE OF CORRECTION

PATENT NO. : 4,203,893
DATED : May 20, 1980
INVENTOR(S) : PIERRE PERY, GERARD LUFFAU, JOELLE POULAIN, AGNES PETIT

It is certified that error appears in the above—identified patent and that said Letters Patent is hereby corrected as shown below:

First page, left-hand column, the inventor "Joelle Polain nee Charley"

should read:

— Joelle Poulain épouse Charley —.

Signed and Sealed this

Thirteenth Day of October 1981

[SEAL]

Attest:

GERALD J. MOSSINGHOFF

Attesting Officer     Commissioner of Patents and Trademarks